United States Patent
Noguchi et al.

(10) Patent No.: US 6,464,677 B1
(45) Date of Patent: Oct. 15, 2002

(54) DISPOSABLE GARMENT

(75) Inventors: Junichi Noguchi; Yoshinori Kumasaka, both of Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/651,110

(22) Filed: Aug. 30, 2000

(30) Foreign Application Priority Data

Aug. 30, 1999 (JP) ............................................ 11-242907

(51) Int. Cl.$^7$ ................................................ A61F 13/15
(52) U.S. Cl. ............................ 604/385.27; 604/385.27; 604/385.26; 604/385.29
(58) Field of Search ...................... 604/385.01, 385.22, 604/385.27, 385.26, 385.29, 398

(56) References Cited

U.S. PATENT DOCUMENTS

| 3,483,864 A | * | 12/1969 | Zacarias ...................... 128/284 |
| 4,585,447 A | * | 4/1986 | Karami ........................ 604/385 |
| 4,895,568 A | * | 1/1990 | Enloe ........................ 604/385.2 |
| 5,019,066 A | * | 5/1991 | Freeland et al. .......... 604/385.2 |
| 5,389,095 A | * | 2/1995 | Suzuki et al. ............. 604/385.2 |
| 5,447,508 A | * | 9/1995 | Numano et al. .......... 604/385.2 |
| 5,593,400 A | * | 1/1997 | O'Leary ................... 604/385.2 |
| 5,690,627 A | * | 11/1997 | Clear et al. .............. 604/385.2 |
| 5,817,087 A | * | 10/1998 | Takabayashi et al. .... 604/385.2 |
| 5,858,012 A | * | 1/1999 | Yamaki et al. ........... 604/385.2 |
| 6,169,225 B1 | * | 1/2001 | Otsubo ........................ 604/361 |
| 6,248,097 B1 | * | 6/2001 | Beitz et al. ............. 604/385.27 |

FOREIGN PATENT DOCUMENTS

| EP | 0404648 | 12/1990 |
| EP | 0601610 | 6/1994 |
| EP | 0763353 | 3/1997 |
| EP | 0904753 | 3/1999 |
| EP | 0933073 | 8/1999 |
| JP | 9-56746 | 4/1997 |
| JP | 9-56747 | 4/1997 |
| WO | WO 95/16421 | 6/1995 |

* cited by examiner

*Primary Examiner*—Aaron J. Lewis
*Assistant Examiner*—Jacqueline F Stephens
(74) *Attorney, Agent, or Firm*—Clark & Brody

(57) ABSTRACT

A disposable garment includes an elastically stretchable outer panel and a body fluid absorbent inner panel. The two panels are connected to each other along front end portions as well as along rear end portions of the panels by means of elastically stretchable connector sheets extending between the front end portions and between the rear end portions of the two panels so that the outer panel may be stretchable together with the connector sheets.

4 Claims, 4 Drawing Sheets

DISPOSABLE GARMENT

BACKGROUND OF THE INVENTION

This invention relates to a disposable garment such as a pants-type or open-type disposable diaper, or training pants.

Japanese Patent Application Disclosure No. 1997-56746 describes a disposable garment comprising a pants-shaped basic structure and a liquid-absorbent pad attached to the inner surface of the basic structure. The basic structure has a first elastically stretchable zone formed in the vicinity of a waist-opening and a second elastically stretchable zone in waist regions extending immediately above a crotch region which is, in turn, stretchable longitudinally of the pants-shaped basic structure. Portions of the pad extending outward beyond its longitudinally opposite ends are respectively joined to longitudinally opposite end portions of the basic structure including said first elastically stretchable zone. The known garment adopts such arrangement and thereby intends to prevent the garment put on a wearer's body from slipping down.

Japanese Patent Application Disclosure No. 1997-56747 describes a disposable garment comprising a pants-shaped basic structure and an absorbent pad attached to the inner surface of the basic structure. Longitudinally opposite end portions of the pad are joined to the basic structure in the vicinity of its waist-opening and the pad is joined at its central zone to a crotch region of the basic structure. This known garment adopts such arrangement and thereby intends to prevent the pad from moving with respect to the basic structure.

A combination of the garment described in the aforesaid Japanese Patent Application Disclosure No. 1997-56746 and the garment described in the aforesaid Japanese Patent Application Disclosure No. 1997-56747 may suggest a garment more or less improved over the article disclosed in respective one of these two documents. The garment suggested hereby comprises a pants-shaped basic structure (corresponding to an outer panel according to this invention) and an absorbent pad (corresponding to an inner panel according to this invention) attached to the inner surface of said basic structure. The basic structure has a first elastically stretchable zone formed in the vicinity of a waist-opening, a second elastically stretchable zone formed in waist regions extending immediately above a crotch region which is, in turn, stretchable longitudinally of the pants-shaped basic structure. The longitudinally opposite end portions of the pad are respectively joined to the longitudinally opposite end portions of the basic structure including the first elastically stretchable zone and the pad is joined at its central zone to the crotch region of the basic structure.

The garment suggested by the combination of these two garments respectively disclosed in the aforesaid Applications may prevent the garment put on a wearer's body with the pad closely placed against the wearer's crotch from slipping down and prevent the pad from floating or shifting sideways with respect to the wearer's crotch.

However, according to this garment suggested by the combination of the two garments, the non-stretchable longitudinally opposite end portions of the pad are respectively joined to the longitudinally opposite end portions of the basic structure. If this operation of joining is carried out with the first elastically stretchable zone being not tensioned, a portion of the first elastically stretchable zone in these joined regions may be prevented from presenting its stretchability. In other words, only the portion of the first elastically stretchable zone lying in the region other than the joined regions cannot present a stretchability sufficient to ensure a desired fitness of the basic structure's waist regions around a wearer's body. On the contrary, if the longitudinally opposite end portions of the pad are respectively joined to the longitudinally opposite end portions with the first elastically stretchable zone being tensioned, contraction of the first elastically stretchable zone may form a plurality of gathers along the longitudinally opposite end portions of the pad. These gathers would come in contact with a wearer's body as the garment is put on and may give the wearer a feeling of incompatibility.

SUMMARY OF THE INVENTION

It is an object of this invention to provide a disposable garment improved so that the waist regions may well fit to the wearer's body under the unrestrained stretchability of the outer panel without creating any feeling of discomfort.

According to this invention, there is provided a disposable garment comprising an elastically stretchable outer panel having transversely opposite side edge portions and longitudinally opposite end portions and a body fluid absorbent inner panel attached to an inner surface of the outer panel and having longitudinally opposite end position, and the outer and inner panels being connected to each other along their front end portions and their rear end portions on the inner surface of the outer panel by means of elastically stretchable connector sheets which extend between the front end portions and between the rear end portions of the two panels, respectively.

The disposable garment according to this invention has the important feature that the outer panel and the inner panel are connected to each other by means of the connector sheets. This unique arrangement is effective to ensure that the outer panel can be stretchable transversely of the garment without being restricted by the inner panel and the waist regions of the garment can be held fit around the wearer's body.

The additional important feature of this invention lies in that the outer panel and the connector sheets are joined together under no tension exerted to these components. Such unique arrangement is effective to avoid a possibility that the outer panel and/or the connector sheets might be formed with gathers and, in consequence, create the wearer a feeling of discomfort.

DETAILED DESCRIPTION OF THE PREFERRED EMBODIMENTS

Details of a disposable garment according to this invention will be more fully understood from the description of a pants-type diaper as one embodiment given hereunder with reference to the accompanying drawings.

Figure 1:
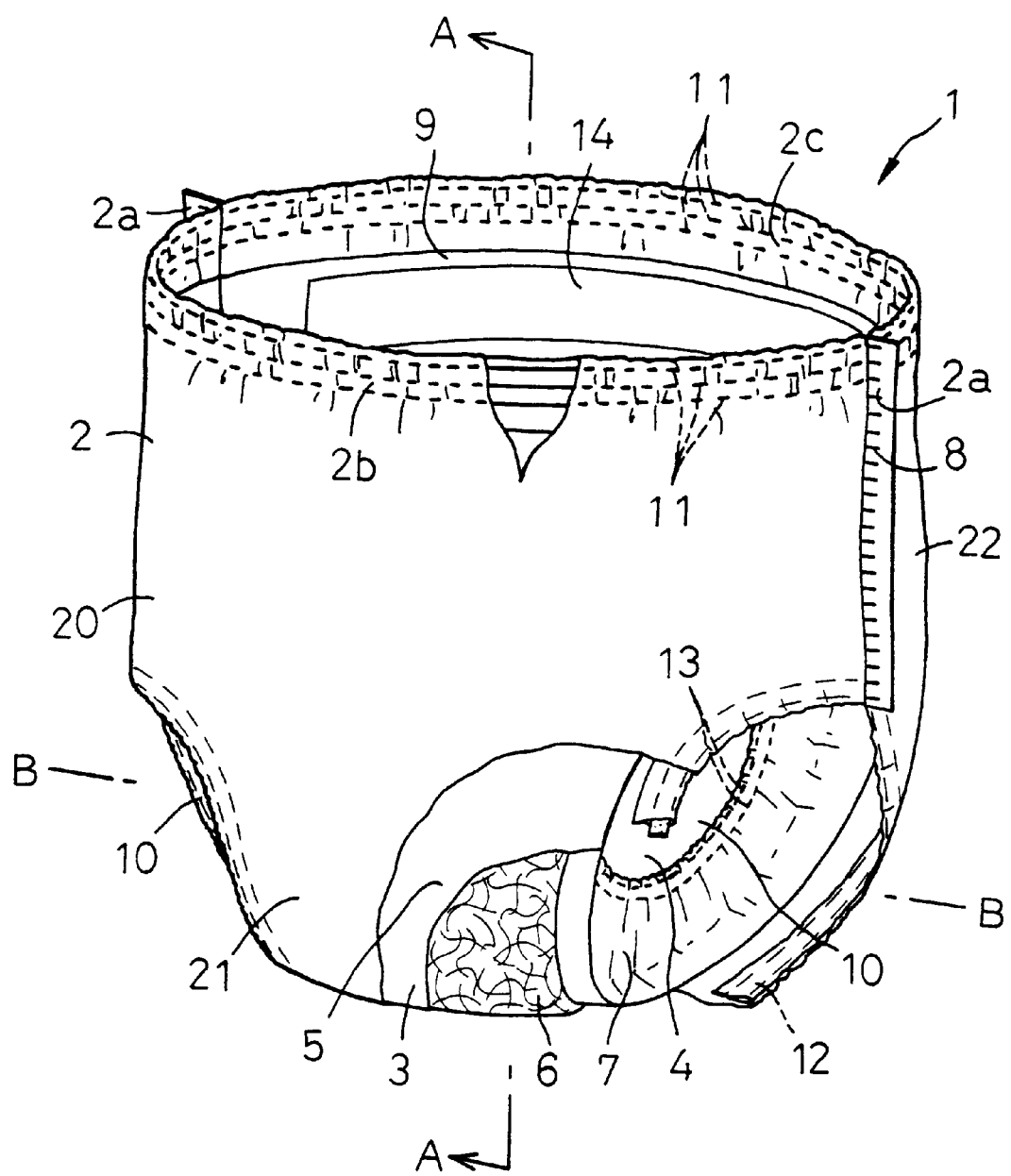
FIG. 1 is a perspective view showing one embodiment of this invention in the form of a disposable pants-type diaper partially cutaway.
Figure 2:
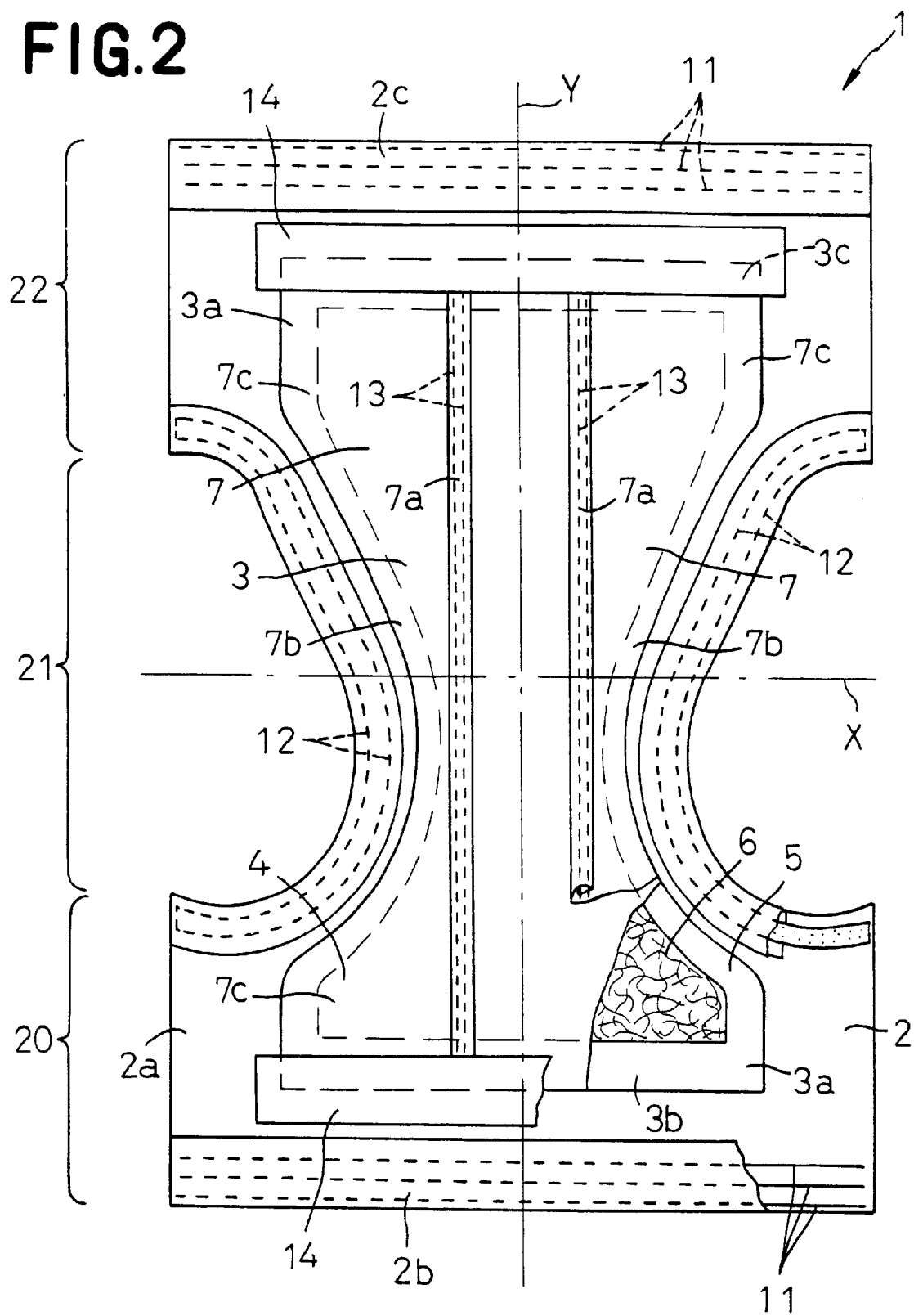
FIG. 2 is a plan view showing the diaper of FIG. 1 as this diaper has been longitudinally developed.

FIG. 1 is a perspective view showing a disposable pants-type diaper partially cutaway and FIG. 2 is a plan view showing the diaper of FIG. 1 as this diaper has been longitudinally developed. The diaper 1 comprises an elastically stretchable outer panel 2 and a body fluid absorbent inner panel 3 attached to the inner surface of the outer panel 2. Configurationally, the diaper 1 is longitudinally composed of a front waist region 20, a rear waist region 22 and a crotch region 21 extending between these front and rear waist region 20, 22. Sections of the outer panel 2 defining the front and rear waist regions 20, 22 are put flat and joined together at a plurality of join spots 8 arranged intermittently along transversely opposite side edge portions 2a of the respective sections. The diaper 1 has a waist-opening 9 defined by longitudinal ends of the front and rear waist regions 20, 22 and a pair of leg-openings 10 defined by transversely opposite side edges of the crotch region 21.

The diaper 1 is provided along the waist-opening 9 with elastic members 11 attached under tension to the diaper 1 and along the leg-openings 10 with elastic members 12 attached under tension to the diaper 1. The elastic members 12 associated with the respective leg-openings 10 respectively are formed with a strip of nonwoven fabric and string elastics joined to the nonwoven fabric and covered with the strip.

The outer panel 2 is hourglass-shaped and contoured by transversely opposite side edge portions 2a, 2a longitudinally extending parallel to each other and longitudinally opposite end portions 2b, 2c transversely extending parallel to each other. The side edge portions 2a, 2a of the outer panel 2 are curved in the crotch region 21 toward a center line Y bisecting a transverse dimension of the diaper 1. The outer panel 2 is cut out along the curved side edge portions 2a, 2a over a smaller area on the side of the front waist region 20 than on the side of the rear waist region 22 around a center line X bisecting a longitudinal dimension of the diaper 1. Namely, the outer panel 2 is configured to be larger on the side of the rear waist region 22 than on the side of front waist region 20.

The inner panel 3 comprises a liquid-pervious topsheet 4, a liquid-impervious backsheet 5 opposed to the inner surface of the outer panel 2 and a liquid-absorbent core 6 disposed between the topsheet 4 and the backsheet 5 and joined between these two sheets 4, 5.

The inner panel 3 is hourglass-shaped and contoured by transversely opposite side edge potions 3a, 3a longitudinally extending parallel to each other and longitudinally opposite end portions 3b, 3c transversely extending parallel to each other. Both the transversely opposite side edge portions 3a, 3a and the longitudinally opposite end portions 3b, 3c are dimensioned to be smaller than those in the outer panel 2. With the inner panel 3 being attached to the inner surface of the outer panel 2, the transversely opposite side edge portions 3a, 3a of the inner panel 3 lie inside the transversely opposite side edge portions 2a, 2a and the longitudinally opposite end portions 3b, 3c lie inside the longitudinally opposite end portions 2b, 2c of the outer panel 2.

The inner panel 3 is provided along its transversely opposite side edge portions 3a, 3a with a pair of barrier cuffs 7, 7 normally biased to rise upwardly of the diaper 1. Each of these cuffs 7, 7 has a free side edge portion 7a longitudinally extending and not joined to the topsheet 4 in the crotch region 21, a fixed side edge portion 7b longitudinally extending parallel to the free side edge portion 7a, and longitudinally opposite end portions 7c, 7c lying on the longitudinally opposite end portions 3b, 3c of the inner panel 3 and joined to the topsheet 4 with said end portions 7c, 7c collapsed inwardly of the inner panel 3 toward the longitudinal center line Y. A longitudinally extending elastic member 13 is secured under tension to the cuff 7 along the free side edge portion 7a.

The inner panel 3 is placed upon and connected to the inner surface of the outer panel 2 by means of connector sheets 14, 14 in a manner that the longitudinally opposite end portions 3b, 3c of the inner panel 3 lie inside the corresponding end portions 2b, 2c of the outer panel 2, respectively, and these end portions 2b, 3b and 2c, 3c are connected one to another by means of the connector sheets 14, 14 transversely extending along and covering these end portions 2b, 3b and 2c, 3c, respectively.

Each of the connector sheets 14, 14 is of single piece type and has substantially no stretchability longitudinally of the diaper 1 but a relatively high stretchability transversely of the diaper 1. The maximum dimension of the connector sheet 14 having been stretched transversely of the diaper 1 is larger than the maximum dimension of the outer panel 2 having been stretched transversely of the diaper 1. A stretch stress of the connector sheet 14 is less than that of the outer panel 2. The connector sheets 14 are joined to the associated end portions 2b, 2c of the outer panels 2 with these two components being under no tension.

The outer panel 2 and the inner panel 3 are connected to each other by means of the connector sheets 14, 14. Consequently, the inner panel 3 does not restrict the stretchability of the outer panel 2 and the latter is kept to be stretchable transversely of the diaper 1 together with the connector sheets 14, 14 in the regions along which the connector sheets 14, 14 are joined to the outer panel 2.

Each of the connector sheets 14, 14 is of a single-piece type and has substantially no stretchability longitudinally of the diaper 1 and it is not apprehended that the respective connector sheets 14, 14 might be longitudinally stretched due to dead load of the inner panel 3 as excretion is discharged on and absorbed by the inner panel 3. It is also not apprehended therefore that the inner panel 3 might hang downwardly of the diaper 1 and the inner panel 3 can be held in close contact with the wearer's body.

Even after the outer panel 2 has been stretched to its maximum length transversely of the diaper 1, the connector sheets 14, 14 can be further stretched because the maximum dimension of the connector sheets 14, 14 having been stretched transversely of the diaper 1 is larger than the maximum dimension of the outer panel 2 having been stretched transversely of the diaper 1. Thus it is not apprehended that the connector sheets 14, 14 might restrain the stretchability of the outer panel 2. In addition, the connector sheets 14, 14 can be more stretchable than the outer panel 2 and it is not apprehended that the stretch stress of these connector sheets 14, 14 might obstruct the stretchability of the outer panel 2 because the stretch stress of the connector sheets 14, 14 are less than that of the outer panel 2. The connector sheets 14, 14 are bonded to the outer panel 2 without any tension exerted to these components. In this way, there is no apprehension that gathers might be formed on the outer panel 2 and/or the connector sheets 14, 14 and create the wearer of the diaper 1 a feeling of discomfort.

Figure 3:
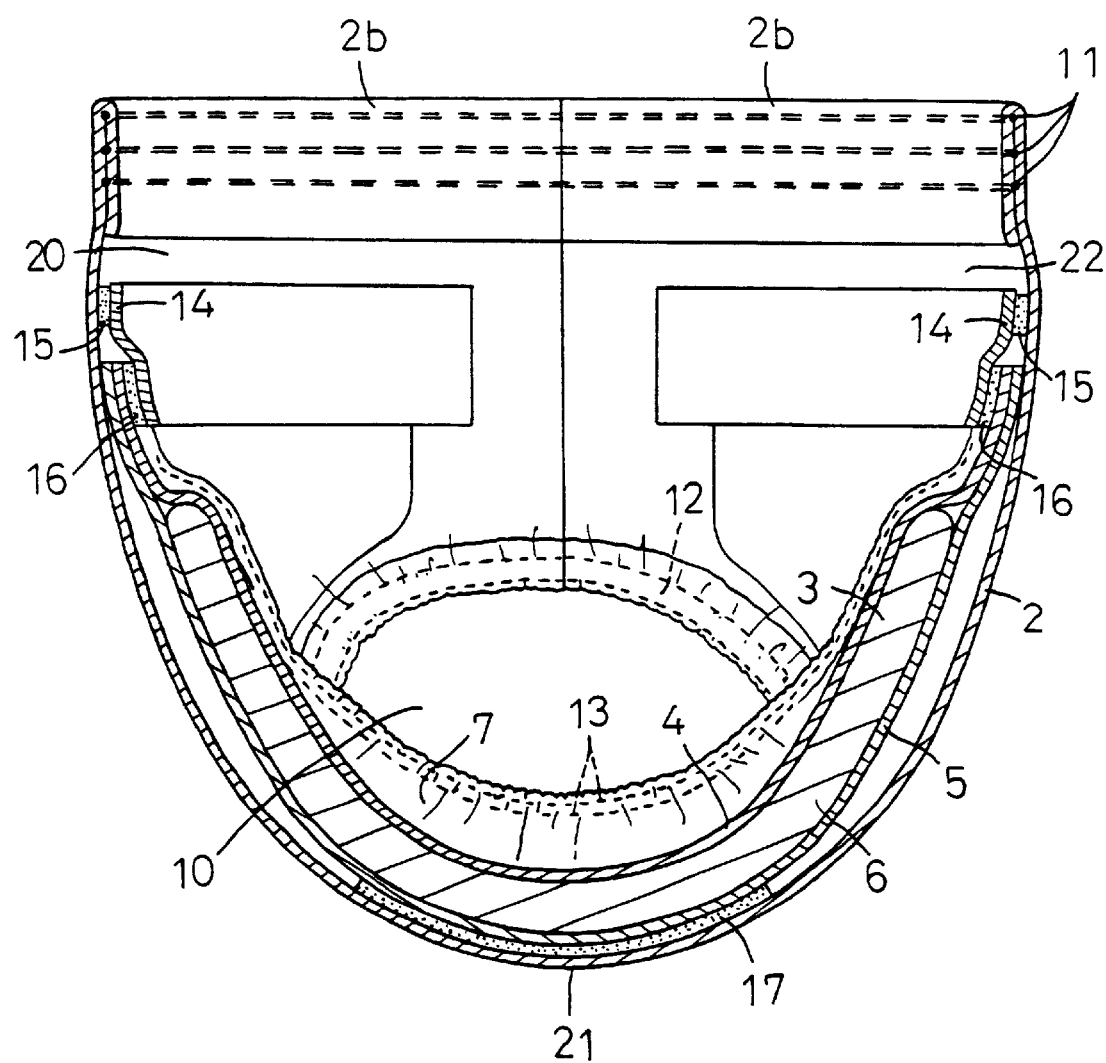
FIG. 3 is a sectional view taken along line A—A in FIG. 1.
Figure 4:
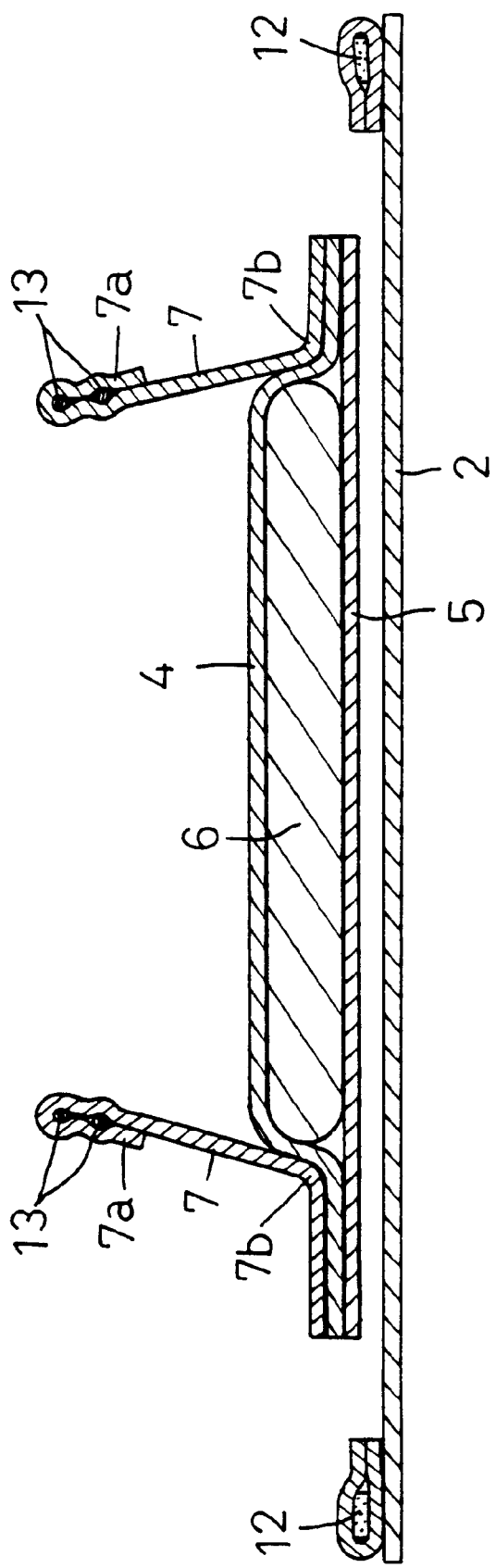
FIG. 4 is a sectional view taken along line B—B in FIG. 1.

FIGS. 3 and 4 are section views taken along line A—A and a line B—B in FIG. 1, respectively. As best seen in FIG. 3, the connector sheets 14, 14 extend between the front end portions 2b, 3b of the outer and inner panels 2, 3 and between the rear end portions 2c, 3c of the outer and inner panels 2, 3, respectively, and are joined to the inner surface of the outer panel 2 and to the topsheet 4 of the inner panel 3 by means of adhesive 15, 16. While it is possible to joined the outer panel 3 to the connector sheets 14, 14 by means of the adhesive 15 continuously applied to them, it is preferable to join the outer panel 3 to the connector sheets 14, 14 by means of the adhesive 15 intermittently applied to them in order to avoid a possibility that the stretchability of these outer panel 3 and connector sheets 14, 14 might be restricted by the adhesive 15.

The inner panel 3 is joined at its longitudinally middle zone to a longitudinally middle zone of the outer panel 2 by means of adhesive 17. The front end portions 2b, 3b as well as the rear end portions 2c, 3c of these panels 2, 3 are not in a relationship of direct connection.

The longitudinally opposite end portions 2b, 2c of the outer panel 2 are partially folded toward the center line X of the diaper 1 onto the inner surface of the outer panel 2 to cover the elastic members 11 associated with the waist-opening 9. In the crotch region 21 of the outer panel 2, the elastic members 12 extend along its transversely opposite side edge portions 2a, 2a and are joined to the inner surface of the outer panel 2. While the outer panel 2 is provided along the front and rear end portions 2b, 2c as well as the side edge portions 2a, 2a in the crotch region 21 with the elastic members 11, 12 in order to prevent the diaper 1 from slipping down along the wearer's body, these elastic members 11, 12 may be eliminated if the outer panel 2 itself is elastically stretchable enough to meet such function.

The inner panel 3 includes the topsheet 4 and the backsheet 5 of which the portions extending outward beyond transversely opposite side edges of the core 5 are joined together and the cuffs 7, 7 of which the fixed side edge portions 7c, 7c extending outside the transversely opposite side edges of the core 4 are bonded to the topsheet 4 and the free edge portions 7a, 7a cover the respective elastic members 13. Referring to FIG. 4, the free edge portions 7a, 7a of the cuffs 7, 7 rise upwardly of the diaper 1 as the elastic members 13 contract longitudinally of the diaper 1.

The inner panel 3 and the outer panel 2 are joined together over the longitudinally middle zones thereof and this unique arrangement is effective to prevent the inner panel 3 from floating in the crotch region and/or shifting sideways during actual use of the diaper 1.

The outer panel 2 may be formed by hydrophobic elastically stretchable nonwoven fabric or a laminated sheet consisting of the hydrophobic elastically stretchable nonwoven fabric and an elastically stretchable plastic film, more preferably by a breathable but liquid-impervious elastically stretchable sheet. The connector sheets 14, 14 may be formed preferably by an elastically stretchable nonwoven fabric but it is also possible to form these connector sheets 14, 14 by elastically stretchable plastic film. The topsheet 4 may be formed by a hydrophobic nonwoven fabric chemically treated to convert it rather hydrophilic, a hydrophilic nonwoven fabric obtained from fiber mixed with a suitable agent to make the nonwoven fabric hydrophilic or a liquid-pervious sheet such as a porous plastic film. The backsheet 5 may be formed by a liquid-impervious plastic film or a laminated sheet consisting of a plastic film and a hydrophobic nonwoven fabric, more preferably by a breathable but liquid-impervious sheet. The cuffs 7, 7 may be formed by a breathable nonwoven fabric, preferably by a breathable but liquid-impervious nonwoven fabric. The nonwoven fabric used for this purpose may be selected from a group including an air-through nonwoven fabric, a spun bond nonwoven fabric, a spun lace nonwoven fabric and a melt blown nonwoven fabric.

The core 6 comprises a mixture of fluff pulp and highly absorptive polymer particles compressed to a desired thickness and entirely covered with a water-pervious sheet (not shown) such as tissue paper.

Steps of joining the core 6 to the sheets 4, 5, attaching the elastic members 11, 12, 13 to the diaper 1 and joining the cuffs 7, 7 to the sheet 4 may be carried out not only using an adhesive agent such as hot melt adhesive or pressure-sensitive adhesive but also using a heat-sealing technique.

In addition to the pants-type diaper, this invention is applicable also to the open-type diaper.

What is claimed is:

1. A disposable garment comprising:
   an elastically stretchable outer panel having transversely opposite side edge portions and longitudinally opposite end portions, and a body fluid absorbent inner panel attached to an inner surface of said outer panel and having transversely opposite side edge portions and longitudinally opposite end portions, and
   said outer and inner panels being connected to each other along their front end portions and their rear end portions on the inner surface of said outer panel by means of elastically stretchable connector sheets which are elastically stretchable transversely of said garment, said elastically stretchable connector sheets covering said front and rear end portions of said inner panel,
   wherein said connector sheets extend transveraely of said garment beyond the transversely opposite side edges portions of said inner panel.

2. A disposable garment according to claim 1, wherein the maximum dimension of said connector sheets having been stretched transversely of the garment is larger than the maximum dimension of the garment and a stretch stress of said connector sheets is lower than a stretch stress of said outer panel.

3. A disposable diaper according to claim 1, wherein said inner panel is provided along the transversely opposite side end portions thereof with elasticized barrier cuffs.

4. A disposable garment according to claim 1, wherein said inner panel comprises a liquid-pervious topsheet, a liquid-impervious backsheet and a liquid-absorbent core disposed there between and wherein said inner panel is joined to said outer panel over longitudinally middle zones of said two panels.

* * * * *